United States Patent
Wegener et al.

(10) Patent No.: US 9,713,669 B2
(45) Date of Patent: Jul. 25, 2017

(54) METHOD FOR SIZED-BASED CELL SEPARATION USING SPINNING MEMBRANE FILTRATION

(71) Applicant: Fenwal, Inc., Lake Zurich, IL (US)

(72) Inventors: Christopher Wegener, Libertyville, IL (US); Bret Olson, Evanston, IL (US); Kyungyoon Min, Kildeer, IL (US)

(73) Assignee: Fenwal, Inc., Lake Zurich, IL (US)

( * ) Notice: Subject to any disclaimer, the term of this patent is extended or adjusted under 35 U.S.C. 154(b) by 516 days.

(21) Appl. No.: 14/140,978

(22) Filed: Dec. 26, 2013

(65) Prior Publication Data

US 2015/0182682 A1     Jul. 2, 2015

(51) Int. Cl.
| | | |
|---|---|---|
| *A61M 1/34* | (2006.01) | |
| *A61M 1/26* | (2006.01) | |
| *B01D 63/16* | (2006.01) | |
| *A61M 1/36* | (2006.01) | |

(52) U.S. Cl.
CPC ............ *A61M 1/3496* (2013.01); *A61M 1/26* (2013.01); *A61M 1/262* (2014.02); *A61M 1/3633* (2013.01); *B01D 63/16* (2013.01); *A61M 1/265* (2014.02); *A61M 2205/3365* (2013.01); *B01D 2315/02* (2013.01)

(58) Field of Classification Search
CPC .. A61M 1/265; A61M 1/3496; A61M 1/3633; A61M 2205/3365; A61M 1/26; A61M 1/262; B01D 2315/02; B01D 63/16
See application file for complete search history.

(56) References Cited

U.S. PATENT DOCUMENTS

| | | | |
|---|---|---|---|
| 4,911,847 A | 3/1990 | Shmidt et al. | |
| 4,923,608 A | 5/1990 | Flottmann et al. | |
| 4,994,188 A | 2/1991 | Prince | |
| 5,194,145 A | 3/1993 | Schoendorfer | |
| 5,401,422 A | 3/1995 | Mignot | |
| 5,464,534 A | 11/1995 | Fischel | |

(Continued)

FOREIGN PATENT DOCUMENTS

| | | |
|---|---|---|
| DE | 3631804 | 3/1988 |
| EP | 0070738 | 1/1983 |
| EP | 0630675 | 12/1994 |

(Continued)

OTHER PUBLICATIONS

European Patent Office; dated Apr. 22, 2015; European Search Report; EP; Application No./Patent No. 14190423.5-1651; Applicant: Fenwal, Inc.; 6 pages.

*Primary Examiner* — John Kim
(74) *Attorney, Agent, or Firm* — Cook Alex Ltd.

(57) ABSTRACT

A method is provided for separating a suspension of cellular material comprising at least two differently-sized cell types using a spinning membrane separator. The method comprises selecting the cell type to be separated by passing through the membrane; determining a concentration of the selected cell type in the suspension; selecting an inlet flow rate for the suspension; selecting a rotational speed for the spinning membrane separator related to one or more of the concentration and relative size of the selected cell type in the suspension; rotating the spinning membrane separator at the selected rotational speed so that the selected cell type tends to migrate to regions of the shear field adjacent the porous membrane; and flowing the suspension through the spinning membrane separator.

14 Claims, 3 Drawing Sheets

(56) References Cited

U.S. PATENT DOCUMENTS 5,543,046 A     8/1996   Van Rijn
6,491,819 B2   12/2002   Prince et al.

FOREIGN PATENT DOCUMENTS

| WO | WO 88/04184 | 6/1988 |
| WO | WO 89/02305 | 3/1989 |
| WO | WO 95/13860 | 5/1995 |
| WO | WO 96/10966 | 4/1996 |

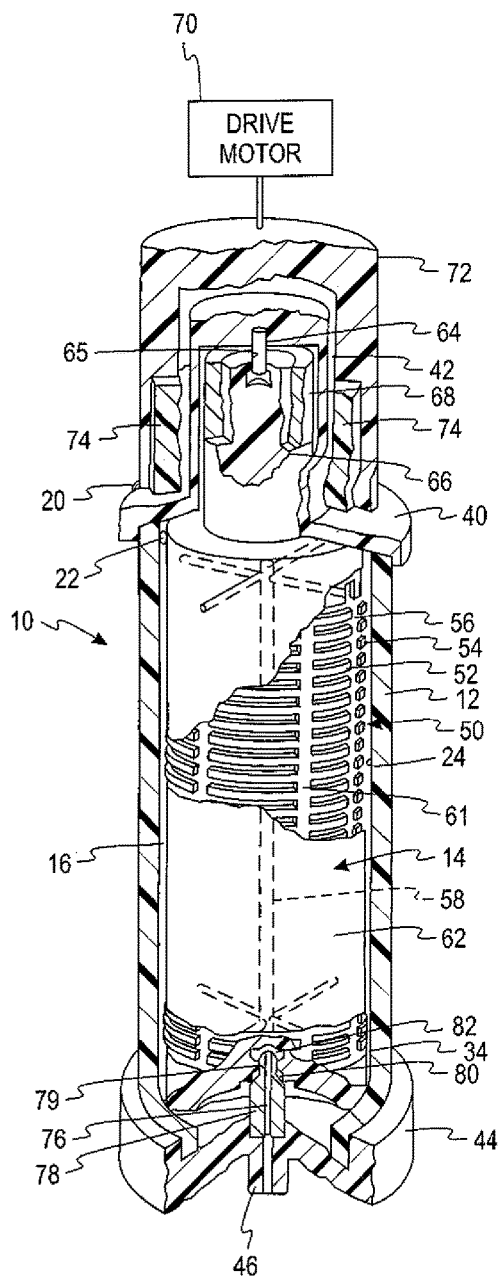
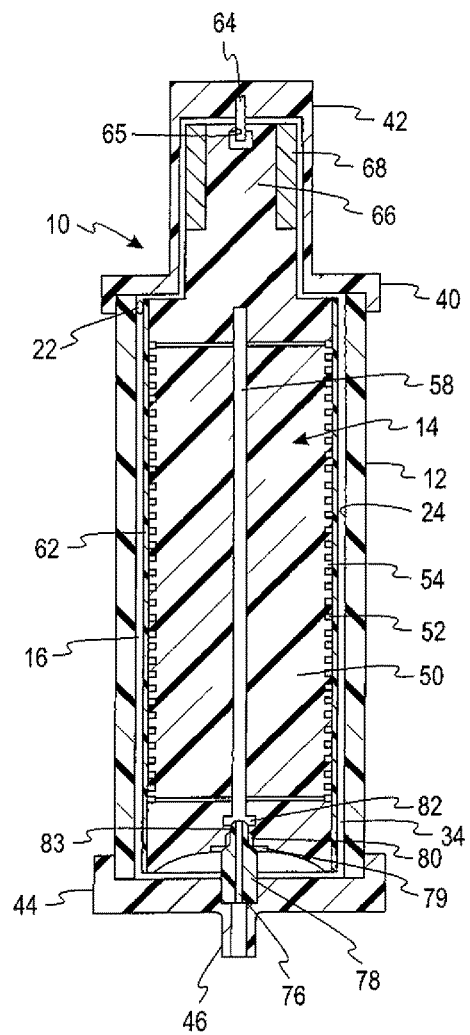
Fig. 1
Fig. 2

| Single Pass Protocols | | |
|---|---|---|
| Source Constituents | Target | Contaminants |
| RBCs + WBCs +PLTs | WBCs | RBCs, PLTs |
| | WBCs, RBCs | PLTs |
| | RBCs, PLTs | WBCs |
| | PLTs | WBCs, RBCs |
| PLTs | PLTs | SRC Supernatant |

*Fig. 4*

| Single Pass Protocol dRBC | | | | | | | |
|---|---|---|---|---|---|---|---|
| Source Constituents | Target | Contaminants | % of Source | | | Recommendations | |
| | | | WBCs | RBCs | PLTs | Flow Rate (mL/min) | Spin Speed (RPM) |
| RBCs + WBCs +PLTs | WBCs | RBCs, PLTs | 81% | 39% | 20% | 100 | 1000-1500 |
| | WBCs, RBCs | PLTs | 88% | 95% | 20% | 150 | >3000 |
| | RBCs, PLTs | WBCs | 19% | 61% | 80% | 150 | 1000-1500 |
| | PLTs | WBCs, RBCs | 12% | 5% | 80% | 150 | >3000 |

*Fig. 5*

| Single Pass Protocol dBC | | | | | | | |
|---|---|---|---|---|---|---|---|
| Source Constituents | Target | Contaminants | % of Source | | | Recommendations | |
| | | | WBCs | RBCs | PLTs | Flow Rate (mL/min) | Spin Speed (RPM) |
| RBCs + WBCs +PLTs | WBCs | RBCs, PLTs | 90% | 45% | 10% | 150 | 1800-2000 |
| | WBCs, RBCs | PLTs | 95% | 83% | 10% | 150 | >3000 |
| | RBCs, PLTs | WBCs | 10% | 55% | 90% | 150 | 1800-2000 |
| | PLTs | WBCs, RBCs | 5% | 17% | 90% | 150 | >3000 |

*Fig. 6*

| Single Pass Protocol MNC | | | | | | | |
|---|---|---|---|---|---|---|---|
| Source Constituents | Target | Contaminants | % of Source | | | Recommendations | |
| | | | WBCs | RBCs | PLTs | Flow Rate (mL/min) | Spin Speed (RPM) |
| RBCs + WBCs +PLTs | WBCs | RBCs, PLTs | 90% | 50% | 22% | 150 | 1400-1600 |
| | WBCs, RBCs | PLTs | 90% | 82% | 55% | 150 | >3000 |
| | RBCs, PLTs | WBCs | 10% | 50% | 78% | 150 | 1400-1600 |
| | PLTs | WBCs, RBCs | 10% | 18% | 45% | 150 | >3000 |

*Fig. 7*

METHOD FOR SIZED-BASED CELL SEPARATION USING SPINNING MEMBRANE FILTRATION

FIELD OF THE DISCLOSURE

The present disclosure relates to a method for separating the cellular components of whole blood using a spinning membrane separator and, more particularly to a method of separating a selected cellular component that is not primarily dependent upon the nominal pore size of the membrane.

BACKGROUND

Spinning porous membrane separators have been used to separate plasma from cellular components of whole blood. A well-known plasmapheresis device is the Plasmacell-C separator sold by Fenwal, Inc. of Lake Zurich, Ill. A detailed description of a spinning membrane separator may be found in U.S. Pat. No. 5,194,145 to Schoendorfer, which is incorporated by reference herein. This patent describes a membrane-covered spinner having an interior collection system disposed within a stationary shell. Blood is fed into an annular space or gap between the spinner and the shell. The blood moves along the longitudinal axis of the shell toward an exit region, with plasma passing through the membrane and out of the shell into a collection bag. The remaining blood components move to the exit region between the spinner and the shell and then are typically returned to the donor.

Spinning membrane separators have been found to provide excellent filtration rates, due primarily to the unique flow patterns ("Taylor vortices") induced in the gap between the spinning membrane and the shell. The Taylor vortices help to sweep the surface of the membrane to inhibit the cellular components, primarily red blood cells, from depositing on and fouling or clogging the membrane.

In membrane filtration, the identity of the filtrate is dependent primarily on size differentiation between the nominal pore size of the membrane and the cellular components of the retentate. For performing plasmapheresis by means of a spinning membrane, the nominal pore size is typically on the order of 0.65 µm, which allows plasma to pass through the membrane while retaining the bulk of the cellular blood components, namely white blood cells ("WBCs"), red blood cells ("RBCs") and platelets ("PLTs"). This retentate remains in the gap between the spinning membrane and the housing, and then exits the spinner housing. Thus, separation of WBCs, RBCs and PLTs from each other would require passing the retentate again through a separation device in which the membrane has a different nominal pore size, e.g., 4.0-5.0 µm, which would permit RBCs to pass through, but retain WBCs.

By way of the present disclosure, methods are provided for separating the various blood components using a spinning membrane separator in which the type of cell that is separated is not solely dependent upon the nominal pore size of the membrane. Consequently, different resultant cell products may be obtained using a single spinning membrane separator.

SUMMARY

The present subject matter has a number of aspects which may be used in various combinations, and a disclosure of one or more specific embodiments is for the purpose of disclosure and description, and not limitation. This summary highlights only a few of the aspects of this subject matter, and additional aspects are disclosed in the drawings and the more detailed description that follows.

A method is provided for separating a suspension of cellular material comprising at least two differently-sized cell types using a spinning membrane separator. The spinning membrane separator comprises a generally cylindrical housing having an interior wall, with an interior member is mounted therein that has an external surface. The interior wall of the housing and/or the external surface of the interior member includes a porous membrane that is spaced apart from the facing wall of the housing or surface of the interior member so as to define an annular gap therebetween. The housing and interior member are relatively rotatable, so that relative rotation of the housing and interior member creates a shear field in the gap having a force gradient, with higher forces adjacent the interior wall of the housing and the external surface of the interior member.

In accordance with one aspect, the method comprises selecting the cell type to be separated by passing through the membrane; determining a concentration of the selected cell type in the suspension; selecting an inlet flow rate for the suspension; selecting a rotational speed for the spinning membrane separator related to one or more of the concentration and relative size of the selected cell type in the suspension; rotating the spinning membrane separator at the selected rotational speed so that the selected cell type tends to migrate to regions of the shear field adjacent the porous membrane; and flowing the suspension through the spinning membrane separator.

In a further aspect, the method comprises selecting the rotational speed so that a higher concentration and/or smaller relative size for the selected cell type results in selection of a higher/faster rotational speed, and a lower concentration and/or larger relative size results in selection of a lower/slower rotational speed.

In another aspect, the method comprises diluting the suspension prior to separation to enhance the susceptibility of the cellular material to segregation by cell type within shear fields formed within the spinning membrane separator.

In further aspect, the method further comprises the spinning membrane separator having a default rotational speed, and adjusting the rotational speed from the default speed to the selected speed.

In a particular application, the suspension comprises red blood cells, white blood cells, platelets and plasma, the spinning membrane separator has a nominal pore size of 4.0-5.0 µm, the selected cell type is red blood cells, and the default rotational speed is 3000 rpm.

BRIEF DESCRIPTION OF THE DRAWINGS

These and other features of the present subject matter are described in the following detailed description and shown in the attached figures, of which:

FIG. 1 is a perspective view of a spinning membrane separator, in partial cross section and with portions removed to show detail.

FIG. 2 is a longitudinal cross sectional view of the spinning membrane separator of FIG. 1.

FIG. 4 is a table identifying five different possible debulking protocols with respect to three different source types (dRBC, dBC, and MNC) that may be performed in accordance with the methods of the present application.

FIGS. 5, 6 and 7 are tables outlining protocols for specific targeted cellular components for dRBC, dBC and MNC products in accordance with the methods of the present application.

DETAILED DESCRIPTION

Figure 3:
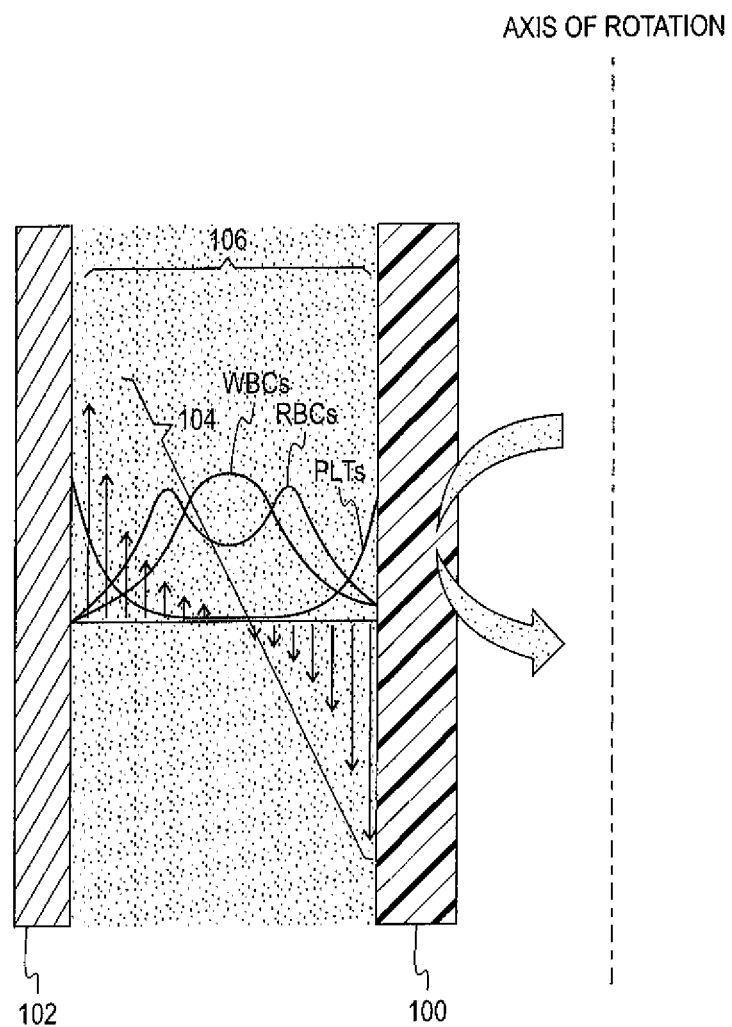
FIG. 3 is a schematic diagram illustrating the shear field in the gap and the relative diffusion of cellular components in the shear field based on size.

A more detailed description of the methods in accordance with the present disclosure is set forth below. It should be understood that the description below of specific devices and methods is intended to be exemplary, and not exhaustive of all possible variations or applications. Thus, the scope of the disclosure is not intended to be limiting, and should be understood to encompass variations or embodiments that would occur to persons of ordinary skill.

Turning to FIGS. 1 and 2, a spinning membrane blood separation or fractionation system, generally designated 10, is shown. Such a system 10 has primarily been used to extract plasma from whole blood obtained from an individual human donor. However, as described in more detail below, the device may also be used for isolating the cellular blood components. For ease of understanding, only the separation device and the associated drive unit are shown, although it should be understood that such a separator forms part of a disposable system including collection bags, bags of additives such as saline or ACD, return bags, tubing, etc., and that there are also associated control and instrumentation systems for operation of the device.

The system 10 includes a generally cylindrical housing 12, mounted concentrically about a longitudinal vertical central axis. An internal member 14 is mounted concentric with the central axis. The housing and internal member is relatively rotatable. In the preferred embodiment, as illustrated, the housing is stationary and the internal member is a rotating spinner that is rotatable concentrically within the cylindrical housing 12. The boundaries of the blood flow path are generally defined by the gap 16 between the interior surface of the housing 12 and the exterior surface of the rotary spinner 14. The spacing between the housing and the spinner is sometimes referred to as the shear gap. A typical shear gap may be approximately 0.025-0.050 inches (0.067-0.127 cm) and may be of a uniform dimension along the axis, for example, where the axis of the spinner and housing are coincident. The shear gap may also vary circumferentially for example, where the axis of the housing and spinner are offset.

The shear gap also may vary along the axial direction, for example preferably an increasing gap width in the direction of flow to limit hemolysis. Such a gap width may range from about 0.025 to about 0.075 inches (0.06-0.19 cm). For example the axes of the housing and rotor could be coincident and the diameter of the rotor decrease in the axial direction (direction of flow) while the diameter of inner surface of the housing remains constant or the diameter of the housing increases while the rotor diameter remains constant, or both surfaces vary in diameter. For example the gap width may be about 0.035 inches (0.088 cm) at the upstream or inlet end of the gap and about 0.059 inches (0.15 cm) at the downstream end or terminus of the gap. The gap width could be varied by varying the outer diameter of the rotor and/or the inner diameter of the facing housing surface. The gap width could change linearly or stepwise or in some other manner as may be desired. In any event, the width dimension of the gap is preferably selected so that at the desired relative rotational speed or speeds, Taylor-Couette flow, such as Taylor vortices, are created in the gap.

Whole blood is fed from an inlet conduit 20 through an inlet orifice 22, which directs the blood into the blood flow entrance region in a path tangential to the circumference about the upper end of the spinner 14. At the bottom end of the cylindrical housing 12, the housing inner wall includes an exit orifice 34.

The cylindrical housing 12 is completed by an upper end cap 40 having an end boss 42, the walls of which are nonmagnetic, and a bottom end housing 44 terminating in a plasma outlet orifice 46 concentric with the central axis.

The spinner 14 is rotatably mounted between the upper end cap 40 and the bottom end housing 44. The spinner 14 comprises a shaped central mandrel or rotor 50, the outer surface of which is shaped to define a series of spaced-apart circumferential grooves or ribs 52 separated by annular lands 54. The surface channels defined by the circumferential grooves 52 are interconnected by longitudinal grooves 56. At each end of the mandrel 50, these grooves 56 are in communication with a central orifice or manifold 58.

In the illustrated embodiment, the surface of the rotary spinner 14 is at least partially, and is preferably substantially or entirely, covered by a cylindrical porous membrane 62. If the system 10 is being used for plasmapheresis, the membrane 62 typically has a nominal pore size of 0.65 microns, but, as described below, other pore sizes may be used if isolation and separation of the cellular blood components is desired. Membranes useful in the methods described herein may be fibrous mesh membranes, cast membranes, track etched membranes or other types of membranes that will be known to those of skill in the art.

The rotary spinner is mounted in the upper end cap to rotate about a pin 64, which is press fit into the end cap 40 on one side and seated within a cylindrical bearing surface 65 in an end cylinder 66 forming part of the rotary spinner 14. The internal spinner or outer housing may be rotated by any suitable rotary drive device or system. As illustrated, the end cylinder 66 is partially encompassed by a ring 68 of magnetic material utilized in indirect driving of the spinner 14. A drive motor 70 exterior to the housing 12 is coupled to turn an annular magnetic drive member 72 that includes at least a pair of interior permanent magnets 74. As the annular drive member 72 is rotated, magnetic attraction between the ring 68 interior to the housing 12 and the magnets 74 exterior to the housing locks the spinner 14 to the exterior drive, causing the spinner 14 to rotate.

At the lower end of the rotary spinner 14, the central outlet orifice 58 communicates with a central bore 76 in an end bearing 78 that is concentric with the central axis. An end bearing seat is defined by an internal shoulder 80 that forms a lower edge of a central opening 82. The central opening 82 communicates with the plasma outlet orifice 46. If the inner facing surface of the housing is covered entirely or partially by a membrane, a fluid collection or manifold may be provided beneath the membrane to collect plasma and direct it through a housing outlet (not shown).

In accordance with the present disclosure, a separation method utilizing a spinning membrane separator is provided in which the nominal pore size of the membrane is selected and the gradient of the shear forces in the gap between the membrane and the housing is manipulated to cause diffusion of the cellular components to be retained in the gap away from the membrane to inhibit transport of that cellular component through the membrane and to enhance passage of the selected cellular component through the membrane. More specifically, the shear gradient is controlled by varying the rotational speed of the membrane relative to the housing by selecting a rotational speed related to one or more of the concentration and relative size of the cell type in the suspension to be passed through the membrane, such that a higher concentration and/or smaller relative size results in selection of a higher/faster rotational speed, and a lower concentration and/or larger relative size results in selection of a lower/slower rotational speed.

As illustrated in FIG. 3, when the membrane 100 is rotated relative to the housing 102, a shear gradient 104 forms across the gap 106 such that the highest shear forces (represented by the longest field lines) are encountered adjacent the surfaces of the membrane and housing, with the shear force theoretically decreasing to zero at the center or midway point of the gap. The principal cellular components of whole blood are, from largest to smallest in size, white blood cells, red blood cells, and platelets. Mature normal RBCS, which have no nucleus and are typically discoid in shape, have a diameter of about 7 µm and a thickness of about 2 µm. Although not perfectly spherical, WBCs typically have an outer diameter of a minimum of about 4.5 µm to about 20 µm, with a nucleus of typically 3.8 to 4 µm or greater. Platelets are discoid in shape and typically 2-3 µm in diameter. When a suspension of cellular blood components is introduced into the gap, the cells will diffuse spatially to minimize their presence in the shear field. Specifically, WBCs, being the largest, will be subjected to the largest shear forces and will be driven to the center of the gap. RBCS, being the next largest, will be driven to the center of the gap to the extent that this space is not already occupied by WBCs. PLTS will have the least force driving them toward the center, and this force is likely to be offset by the larger cells already occupying this space.

The shape and size of the pores in the membrane, as well as the spacing between the pores, can be selected depending on the identity of the cellular components to be passed through, and the relative deformability of the different cell types may be taken into account. For example, it is known that normal RBCS are relatively more readily deformable than WBCs, and deform faster and under less force than WBCs. Thus, if a nominal pore size of 4.0 µm-5.0 µm is selected for the membrane, WBCs will be retained and RBCS and PLTs can pass through the membrane. Accordingly, by appropriate selection of the rotational speed of the membrane the bulk of the PLTS and/or the bulk of the RBCS can each be separated from the bulk of the WBCs. For example a suspension of WBCs, RBCS and PLTS could be introduced into the gap of the spinning membrane separator, and the rotational speed selected so that the bulk of the WBCs and RBCS are maintained in the center of the gap to first separate the PLTS (with minimal RBCS) by passing through the membrane. Then the rotational speed adjusted (reduced) to cause the RBCS to migrate toward the membrane to separate the bulk of the RBCS from the WBCs by passing the RBCS through the membrane, while the WBCs are maintained in the gap. Depending on the relative concentrations of the various cellular components in the suspension, it may be necessary to dilute the suspension (with, e.g., saline) to lower the concentrations and thus enhance the susceptibility of the cellular components to segregation by cell type when subjected to the shear field. Thus, a single spinning membrane separator, appropriately controlled, could be used to obtain concentrations of each of WBCs, RBCS and PLTs.

The method may also be advantageously used for various "single pass" separation protocols, including debulking or WBC removal (where WBCs are retained, and RBCS and PLTs are passed through the membrane), platelet removal (where WBCs and RBCS are retained, and PLTs passed through the membrane), WBC removal (where WBCs are retained and RBCS and PLTs passed through the membrane), washing operations (where a source supernatant is replaced with a new medium while retaining all of the cells within the source product), and isolation of a single cell-type product from a WBC/RBC cell suspension or from a RBC/PLT cell suspension.

Specifically, the method according to the present disclosure controls three variables to selectively separate selected cellular components using a spinning membrane separator, namely inlet flow rate, the source product composition, and the membrane spin speed. Testing was performed to establish various single pass protocols. Five different debulking protocols, as set forth in Table 4, were established with respect to three different source types: diluted RBCS (dRBC), diluted buffy coat (dBC), and mononuclear cells (MNCs). It should be appreciated that the five identified protocols are only a subset of all the plausible protocols, and are presented herein for purposes of illustration, and not limitation.

Protocols were established using a spinning membrane separator as described above having a PCTE membrane with a nominal pore size of 4.0 µm. In establishing the flow rates and spin speeds for the protocols, minimum retention levels for the various cellular components are set. It has been determined that flow rates become a factor in WBC retention at speeds lower than 2000 rpm, with WBC retention being highest at flow rates of 50 mL/min and lowest at 150 ml/min. Flow rates become a factor in RBC retention at speeds lower than 2500 rpm, where slower flow rates lead to higher RBC retention (similar to WBCs). Platelets behave differently than WBCs and RBCS, in that flow rate and spin speed do not appear to affect PLT retention, which is approximately 20%. FIGS. 5, 6 and 7 outline protocols for specific targeted cellular components for dRBC, dBC and MNC products, specifying the target cells and contaminants, the percentage of the source retained by cell type, the flow rate and spin speed.

Thus, this can be seen from the above description, the present disclosure has several different aspects which are not limited to the specific methods and apparatus shown in the attached drawings or described above. Variations of these concepts may be embodied in other steps for carrying out the methods and apparatus without departing from the scope of the disclosure.

Aspects of the present subject matter described above may be beneficial alone or in combination with one or more other aspects. Without limiting the foregoing description, in accordance with one aspect of the subject matter herein, there is provided In accordance with one aspect, the method comprises selecting the cell type to be separated by passing through the membrane; determining a concentration of the selected cell type in the suspension; selecting an inlet flow rate for the suspension; selecting a rotational speed for the spinning membrane separator related to one or more of the concentration and relative size of the selected cell type in the suspension; rotating the spinning membrane separator at the selected rotational speed so that the selected cell type tends to migrate to regions of the shear field adjacent the porous membrane; and flowing the suspension through the spinning membrane separator.

In a further aspect, the method comprises selecting the rotational speed so that a higher concentration and/or smaller relative size for the selected cell type results in selection of a higher/faster rotational speed, and a lower concentration and/or larger relative size results in selection of a lower/slower rotational speed.

In another aspect, the method comprises diluting the suspension prior to separation to enhance the susceptibility of the cellular material to segregation by cell type within shear fields formed within the spinning membrane separator.

In further aspect, the method further comprises the spinning membrane separator having a default rotational speed, and adjusting the rotational speed from the default speed to the selected speed.

In a particular application, the suspension comprises red blood cells, white blood cells, platelets and plasma, the spinning membrane separator has a nominal pore size of 4.0-5.0 μm, the selected cell type is red blood cells, and the default rotational speed is 3000 rpm.

The invention claimed is:

1. A method for separating a suspension of cellular biological material comprising at least two differently-sized cell types using a spinning membrane separator, the steps comprising:
   a) selecting the cell type to be separated by passing through the membrane;
   b) determining a concentration of each different cell type in the suspension;
   c) selecting an inlet flow rate for the suspension;
   d) selecting a rotational speed for the spinning membrane separator related to the concentration and size of the selected cell type in the suspension relative to each non-selected cell type;
   e) rotating the spinning membrane separator at the selected rotational speed; and
   f) flowing the suspension through the spinning membrane separator.

2. The method of claim 1 wherein the rotational speed of the spinner is selected such that a higher relative concentration and/or smaller relative size of the selected cell type results in selection of a higher/faster rotational speed and a lower relative concentration and/or larger relative size of the selected cell type results in selection of a lower/slower rotational speed.

3. The method of claim 1 wherein the suspension is diluted prior to separation to enhance the susceptibility of the cellular material to segregation by cell type within shear fields formed within the spinning membrane separator.

4. The method of claim 1 further comprising the spinning membrane separator having a default rotational speed and adjusting the rotational speed from the default speed to the selected speed.

5. The method of claim 4 wherein the suspension comprises red blood cells, white blood cells, platelets and plasma, the spinning membrane separator has a pre-determined nominal pore size and the selected cell type is red blood cells.

6. The method of claim 5 wherein the nominal pore size is 4 μm and the default rotational speed is 3000 rpm.

7. The method according to claim 1, wherein the suspension of cellular biological material comprises at least two of red blood cells, white blood cells and platelets, the spinning membrane separator has a pre-determined nominal pore size, and the selected cell type is one of the at least two of red blood cells, white blood cells and platelets.

8. A method for separating a suspension of cellular biological material comprising at least two differently-sized cell types using a spinning membrane separator comprising a generally cylindrical housing having an interior wall; an interior member mounted interior of the housing and having an external surface; the interior wall of the housing and/or the external surface of the interior member including a porous membrane spaced apart from the facing wall of the housing or surface of the interior member so as to define an annular gap therebetween; the housing and interior member being relatively rotatable; wherein relative rotation of the housing and interior member creates a shear field in the gap having a force gradient with higher forces adjacent the interior wall of the housing and the external surface of the interior member, the steps comprising:
   a) selecting the cell type to be separated by passing through the membrane;
   b) determining a concentration of each different cell type in the suspension;
   c) selecting an inlet flow rate for the suspension;
   d) selecting a rotational speed for the spinning membrane separator related to the concentration and size of the selected cell type in the suspension relative to each non-selected cell type;
   e) rotating the spinning membrane separator at the selected rotational speed so that the selected cell type tends to migrate to regions of the shear field adjacent the porous membrane; and
   f) flowing the suspension through the spinning membrane separator.

9. The method of claim 8 wherein the rotational speed of the spinner is selected such that a higher relative concentration and/or smaller relative size of the selected cell type results in selection of a higher/faster rotational speed and a lower relative concentration and/or larger relative size of the selected cell type results in selection of a lower/slower rotational speed.

10. The method of claim 8 wherein the suspension is diluted prior to separation to enhance the susceptibility of the cellular material to segregation by cell type within the shear field formed in the gap within the spinning membrane separator.

11. The method of claim 8 further comprising the spinning membrane separator having a default rotational speed and adjusting the rotational speed from the default speed to the selected speed.

12. The method of claim 11 wherein the suspension comprises red blood cells, white blood cells, platelets and plasma, the spinning membrane separator has a pre-determined nominal pore size, and the selected cell type is red blood cells.

13. The method of claim 12 wherein the nominal pore size is 4 μm and the default rotational speed is 3000 rpm.

14. The method according to claim 8, wherein the suspension of cellular biological material comprises at least two of red blood cells, white blood cells and platelets, the spinning membrane separator has a pre-determined nominal pore size, and the selected cell type is one of the at least two of red blood cells, white blood cells and platelets.

* * * * *